United States Patent [19]

Lee et al.

[11] 4,374,067
[45] Feb. 15, 1983

[54] INTERMEDIATES FOR THE PREPARATION OF 4-PHENYL-1,3-BENZODIAZEPINS AND METHODS FOR PREPARING THE INTERMEDIATES

[75] Inventors: Thomas B. K. Lee, Whitehouse Station; George E. Lee, Somerville, both of N.J.

[73] Assignee: Hoechst-Roussel Pharmaceuticals, Inc., Somerville, N.J.

[21] Appl. No.: 333,965

[22] Filed: Dec. 23, 1981

[51] Int. Cl.³ .................. C07C 143/68; C07C 125/06; C07C 103/127
[52] U.S. Cl. .................... 260/456 A; 260/239 BD; 560/27; 564/219; 564/221
[58] Field of Search .................... 560/27; 260/456 A; 564/221, 219

[56] References Cited

U.S. PATENT DOCUMENTS 4,182,760  1/1980  Middleton .......................... 564/221

OTHER PUBLICATIONS

Muchowski et al., J. Org. Chem., 45, 4798 (1980).
Fuhrer et al., J. Org. Chem., 44, 1133 (1979).

*Primary Examiner*—Nicky Chan

[57] ABSTRACT

The invention relates to compounds of the formula

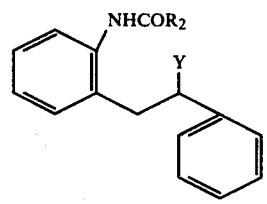

where Y is —OH; halogen;

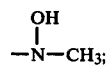

$R_1SO_3$—, where $R_1$ is a straight chain or branched chain alkyl group having 1 to 5 carbon atoms, or aryl; and $R_2$ is —$C(CH_3)_3$ or —O—$C(CH_3)_3$. Processes for preparing the compounds are provided. The compounds are useful as intermediates in the preparation of 4-phenyl-1,3-benzodiazepins, which exhibit activity as antidepressants, analgetics and anticonvulsants.

8 Claims, No Drawings

INTERMEDIATES FOR THE PREPARATION OF 4-PHENYL-1,3-BENZODIAZEPINS AND METHODS FOR PREPARING THE INTERMEDIATES

The present invention relates to intermediates for the preparation of 4-phenyl-1,3-benzodiazepins, and in particular intermediates for the synthesis of the compound 4,5-dihydro-2,3-dimethyl-4-phenyl-3H-1,3-benzodiazepin, and its optical antipodes and physiologically acceptable salts.

The compound 4,5-dihydro-2,3-dimethyl-4-phenyl-3H-1,3-benzodiazepin has the formula

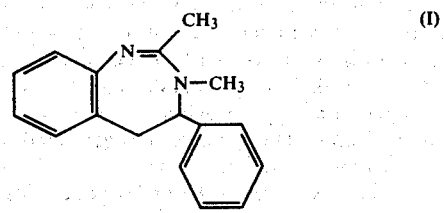

This compound, its optical antipodes and physiologically acceptable salts are useful as antidepressants, analgetics and anticonvulsants. Of particular interest for these purposes are the hydrochloride salts of the 4-phenyl-1,3-benzodiazepin of formula (I).

The 4-phenyl-1,3-benzodiazepins, methods for their preparation and compounds useful as intermediates in their preparation are known. The known methods of preparation require a relatively large number of steps, the steps are relatively complicated, the starting materials are costly and the yields of the 4-phenyl-1,3-benzodiazepins are less than desirable.

This invention provides novel intermediate compounds utilized in the preparation of the 4-phenyl-1,3-benzodiazepins of formula (I). These intermediates have the formula

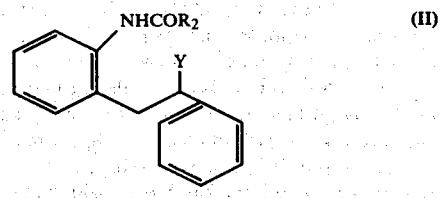

where Y is —OH; halogen;

$R_1SO_3$—; where $R_1$ is a straight chain or branched chain alkyl group having 1 to 5 carbon atoms, or aryl; and $R_2$ is —C(CH$_3$)$_3$ or —O—C(CH$_3$)$_3$.

This invention also provides methods for preparing the compounds of the invention.

In addition, this invention provides for the use of the compounds of the invention in the preparation of the 4-phenyl-1,3-benzodiazepins of formula (I).

When the compounds of the invention are utilized in the synthesis of the 4-phenyl-1,3-benzodiazepins of formula (I), a smaller number of process steps may be employed, and the benzodiazepins may be prepared in high yields and increased purity.

Preferred compounds of the invention are those in which the substituent Y is hydroxyl, chlorine or bromine. When Y is halogen, chlorine is particularly preferred. When Y in formula (II) is $R_1SO_3$— and $R_1$ is alkyl, a methyl sulfonyl group is preferred. As used throughout the specification and appended claims, the term "alkyl" shall mean an acyclic hydrocarbon group containing no unsaturation. When Y in formula (II) is $R_1SO_3$— and $R_1$ is aryl, the substituent group will typically be a phenyl sulfonyloxy, a p-chlorophenyl sulfonyloxy or a p-toluene sulfonyloxy group.

The compounds of formula (I) and the compounds of formula (II) can be prepared according to the following sequence of reactions.

1. An N-acylated-o-toluidine of the formula

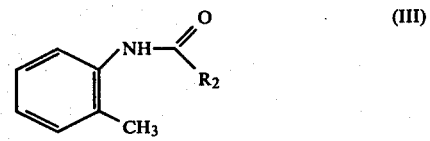

is converted to a dilithio intermediate of the formula

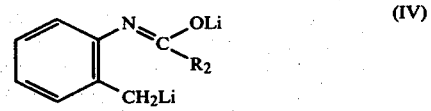

where $R_2$ is as defined above. The N-acylated-o-toluidine of formula (III) is N-[(2-methyl)-phenyl]-2,2-dimethylpropanamide or N-t-butoxycarbonyl-o-toluidine. Lithiation of aromatic compounds with an n-alkyllithium compound is exemplified in J. M. Muchowski and M. Venturi, J. Org. Chem. 45, 4798–4801 (1980) and W. Fuhrer and H. W. Gschwend, J. Org. Chem. 44, 1133–1136 (1979). A preferred method according to the present invention involves slowly adding a solution of alkyllithium, such as n-butyllithium, sec-butyllithium or tert-butyllithium, in a solvent therefor, such as hexane, to a solution of the N-acylated-o-toluidine in an ethereal solvent, such as diethyl ether, tetrahydrofuran, dimethoxyethane, and a hydrocarbon solvent, such as hexane. The preferred alkyllithium compound is n-butyllithium. The ethereal solvent and hydrocarbon solvent should be substantially inert to the alkyllithium to avoid adverse side reactions. The temperature during the addition can range from about −70° C. to about 30° C., preferably about −10° C. to about 30° C. The resulting mixture is aged from about one-half to about 5 hours, preferably about 1 to about 2 hours. The reaction is conveniently carried out at atmospheric pressure. The amount of alkyllithium employed is up to about 10% in excess of the 2 molar equivalents required for the reaction. It is important to exclude moisture from the reaction mixture. Accordingly, the reaction is conveniently conducted in an atmosphere of a substantially dry gas, such as substantially anhydrous nitrogen.

2. In order to prepare a compound of formula (II) in which Y is a hydroxyl group, the dilithio intermediate of formula (IV) is quenched with benzaldehyde as an electrophile. The aqueous work up of the reaction mixture provides the compound of formula (II) in which Y is hydroxyl. The temperature of addition of the benzaldehyde can range from about −78° C. to about 35° C., preferably from about 0° to about 25° C. The mixture is aged for a period of about 5 minutes to about one hour. The amount of benzaldehyde employed is from about one to about 2 molar equivalents based on the dilithio intermediate of formula (IV). The quenching with benzaldehyde is conveniently conducted at atmospheric pressure and in a substantially dry e.g., dry nitrogen, atmosphere.

In order to prepare a compound of formula (II) in which Y is halogen, a compound of formula (II) in which Y is hydroxyl is carefully halogenated to provide the corresponding halide. This conversion can be conveniently performed by any method known in the art for converting a benzylic alcohol to the corresponding halide. For instance, a compound according to formula (II) in which Y is a hydroxyl group can be dissolved in a suitable solvent therefor. Typical solvents are non-hydroxylic solvents, such as non-hydroxylic halogenated solvents, or non-nucleophilic amines, such as pyridine or a tertiary amine, such as trimethyl amine. Reaction with about 1 to about 2 equivalents, preferably about 1.1 equivalents, of thionyl chloride at about 0° to about 50° C., preferably about 20° to about 30° C., can be carried out for a period of about 1 to about 16 hours. Other known chlorinating agents, such as phosphorus oxychloride or phosphorus pentachloride can also be employed. The method selected should not result in hydrolysis of the propanamide group or the N-(t-butoxycarbonyl) group. For example, the hydroxy compound can alternatively be reacted with a phosphorus trihalide, such as phosphorus tribromide, under standard reaction conditions. In a preferred method according to this invention, a compound of formula (II) in which Y is hydroxyl is preferably at least partially dissolved in a solvent, such as methylene chloride or pyridine, and then chlorinated by reaction with thionyl chloride. Preferably, the thionyl chloride is employed in about a 10% stoichiometric excess. The reaction is mildly exothermic and can be carried out with additional heating until substantially complete as evidenced by cessation in evolution of sulfur dioxide and hydrogen chloride. The resulting halide can be recovered and purified using conventional techniques.

If a compound of formula (II) in which Y is a hydroxyl group is reacted with an appropriate alkyl or aryl sulfonyl chloride or alkyl or aryl sulfonyl anhydride, it is possible to prepare compounds according to formula (II) in which Y is $R_1SO_3$— as previously defined. For example, reaction of the hydroxy compound (II) with an alkyl sulfonyl chloride, such as methane sulfonyl chloride, will yield a compound of formula (II) in which Y is an alkyl sulfonyl group. Similarly, reaction of the hydroxy compound (II) with phenyl sulfonyl chloride or anhydride, p-chlorophenyl sulfonyl choride or anhydride or p-toluene sulfonyl choride or anhydride will yield the corresponding aryl sulfonates. These reactions can be carried out by employing well-known conditions for reacting hydroxy compounds with alkyl or aryl sulfonyl chlorides and anhydrides to form the corresponding alkyl and aryl sulfonates. Typically, the hydroxy compound of formula (II) in ethereal or hydrocarbon solvents can be reacted with alkyl or aryl sulfonyl chlorides or alkyl or aryl sulfonyl anhydrides at a temperature of about −10° C. to about 70° C., preferably at a temperature of about 0° C. to about 40° C.

Compounds according to formula (II) in which Y is $$\begin{array}{c} \text{OH} \\ | \\ -\text{N}-\text{CH}_3 \end{array}$$

can be prepared by quenching the dilithio intermediate of formula (IV) with an appropriate nitrone. More particularly, the temperature of addition of the nitrone can range from about −78° C. to about 35° C., preferably from about 0° to about 25° C. The mixture is aged for a period of about 5 minutes to about one hour. The amount of nitrone employed is from about one to about 2 molar equivalents based on the dilithio intermediate of formula (IV). In a preferred method according to the invention, the dilithio intermediate of formula (IV) is reacted with about a stoichiometric amount of α-phenyl-N-methyl nitrone at about 0° C. to about 25° C. The quenching is conveniently conducted at atmospheric pressure and in a substantially moisture-free, e.g., dry nitrogen, atmosphere. After aqueous work up, the resulting compound can then be recovered and purified using conventional techniques.

3. The next stage in the preparation of the 4-phenyl-1,3-benzodiazepins of formula (I) is to convert the intermediate of formula (II) into a 2-methylamino-substituted compound having the formula

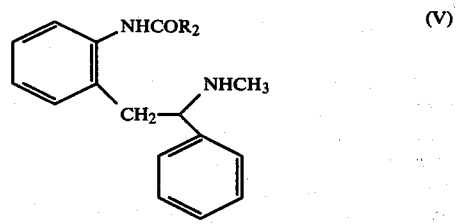

and the chemical name N-[2-(2-methylamino-2phenylethyl)phenyl]-2,2-dimethylpropanamide, when $R_2$ is —C(CH$_3$)$_3$, and the name N-(t-butoxycarbonyl)-2-(2-methylamino-2-phenylethyl)aniline, when $R_2$ is —O—C(CH$_3$)$_3$. This conversion can be carried out as follows. When the substituent Y in formula (II) is a hydroxyl group, the compound is first converted to the corresponding halide or alkyl or aryl sulfonate as described above. The halide or alkyl or aryl sulfonate is reacted with monomethyl amine. The reaction can be carried out in a solvent, such as 2-propanol, at a temperature of about 80° to about 120° C. The reaction can be conducted for about 1 to about 12 hours at a pressure of about 1 atmosphere to about 100 psi. The amount of monomethyl amine will typically be about 1 to about 10 molar equivalents based on the halide or sulfonate of formula (II). A large excess of monomethylamine is preferably employed to ensure substantially complete conversion to the 2-methylamine-substituted compound of formula (V).

When the substituent Y in formula (II) is

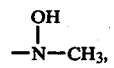

the 2-methylamine-substituted compound of formula (V) can be prepared by reduction of an N-methyl hydroxylamine of formula (II) with a noble metal catalyst, such as platinum or palladium. For example, an N-methyl hydroxylamine of formula (II) can be reacted in methanol and in the presence of hydrogen gas with a palladium on carbon catalyst. The reaction can generally be carried out at about room temperature and atmospheric pressure until substantially complete. The reaction time will typically be about one hour.

An alternate method of preparing the compound of formula (V) via alkyl and aryl sulfonates is as follows. The dilithio intermediate of formula (IV) is quenched with benzaldehyde as described in stage 2 above. Instead of working up the reaction mixture in aqueous phase at the end of the reaction, an alkyl or aryl sulfonic anhydride is added to the reaction mixture. For example, about 1 to about 2 equivalents of methane sulfonic anhydride can be added to the reaction mixture. The resulting reaction is carried out at about 0° to about 20° C. until substantially complete, which will typically be about 30 minutes to about 1 hour. An alkyl or aryl sulfonate intermediate is formed, which can be converted to the compound of formula (V) by reaction with monomethyl amine. More particularly, monomethyl amine can be bubbled into the reaction mixture containing the sulfonate intermediate. The amine should be added slowly to avoid side reactions. Typically, about 3 to about 5 equivalents of monomethyl amine are added during the course of the reaction. The reaction can be carried out at about 0° to about 80° C., preferably at about 0° to about 20° C., until complete, typically for about 1 to about 2 hours. The compound of formula (V) can then be recovered from the reaction mixture and purified using conventional techniques.

4. The compound of formula (V) is then hydrolyzed to provide an N-methyl-2-amino-α-phenylphenethylamine as a free base of the formula

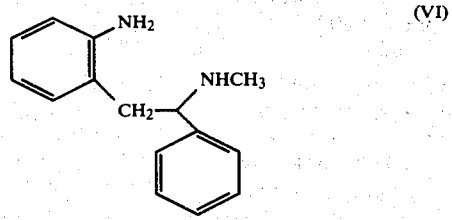

(VI)

or as its salt, e.g., dihydrochloride. The aromatic amine of formula (VI) is the immediate precursor of the 4-phenyl-1,3-benzodiazepins of formula (I). Thus, it will be understood that the salts of the compound of formula (VI) can in general be the same as the salts of the compounds of formula (I).

In one method, the compound of formula (V) is reacted with about 2 molar equivalents of a strong mineral acid, such as hydrochloric acid, hydrobromic acid or sulfuric acid, 6 N hydrochloric acid is the acid of choice. The reaction is conveniently conducted at atmospheric pressure and at a temperature of from about 70° to the reflux temperature of the solvent employed in the reaction for a period of about 12 to about 48 hours to provide a diacid salt, which can then be recrystallized. A solvent, such as ether or an aromatic solvent, is employed to remove any side products while retaining the diacid salt in aqueous phase. If desired, the diacid salt can be basified to provide the free base.

5. The aromatic amine of formula (VI) in free base or salt form can be cyclized with a compound of the formula

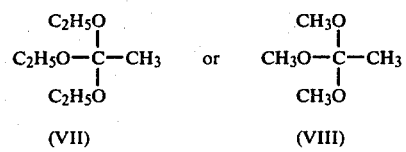

to provide the 4-phenyl-1,3-benzodiazepins of formula (I). This cyclization can be carried out in the presence of an acid catalyst, such as ethanolic hydrochloric acid. Alternatively, the monoacid or diacid salt of the compound of formula (VI) can be cyclized with a compound of formula (VII) or formula (VIII) in a polar solvent, such as acetonitrile or acetic acid. Use of acetonitrile makes it unnecessary to add an acid catalyst to the reaction mixture. The reaction can be conducted at a temperature of from about 25° C. to the reflux temperature of the reaction mixture and at atmospheric pressure for at least about 1 hour, typically about 1 to about 8 hours. About 1 to about 5 molar equivalents, preferably about 2 molar equivalents, of the compound of formula (VII) or formula (VIII) are employed.

The invention is described in greater detail in the following examples in which all parts, proportions, ratios and percentages are by weight unless otherwise indicated.

EXAMPLE 1

Synthesis of trimethylacetyl chloride

A solution of trimethylacetic acid (204.3 g, 2.0 mol) in methylene chloride (400 ml) containing a catalytic amount of DMF (0.5 g) was stirred under a dry nitrogen atmosphere and treated with $SOCl_2$ (258 g, 2.06 mol). Following the addition of $SOCl_2$ (about 5 minutes) the reaction temperature dropped from 21° C. to 13° C.; at the same time, a vigorous evolution of HCl and $SO_2$ occurred. After 5 hours, the reaction was heated to reflux and maintained at this temperature for 2 hours. At this time, the conversion of trimethylacetic acid to trimethylacetyl chloride was quantitative. The crude product, without concentration or distillation, can be employed directly in the synthesis of N-[(2-methyl)-phenyl]-2,2-dimethyl propanamide.

EXAMPLE 2

Synthesis of N-[(2-methyl)phenyl]-2,2-dimethyl propanamide (a) A biphasic solution of o-toluidine (107.2 g, 1.0 mol) in methylene chloride (500 ml) and water (150 ml) containing sodium carbonate (69 g, 0.65 mol) was treated with trimethylacetyl chloride (120.6 g, 1.0 mol). The rate of addition of trimethylacetyl chloride was adjusted so as to maintain the reaction at gentle reflux. After 45 minutes the addition was complete. The organic layer was separated, washed with water, and concentrated in vacuo. The crude N-[(2-methyl)-phenyL]-2,2-dimethylpropanamide was slurried in 2% aqueous HCl, filtered and washed with $H_2O$ until the filtrate was neutral. After drying in vacuo (50° C., 20 mm), N-[(2-methyl)phenyl]-2,2-dimethylpropanamide (178 g, 0.93 mol) was obtained in 93% yield (m.p. 109°-110° C.).

(b) A biphasic solution of o-toluidine (214.4 g, 2.0 mol) in methylene chloride (200 ml) and water (250 ml) containing sodium carbonate (117 g, 1.1 mol) was treated with trimethylacetyl chloride (about 2.0 mol in methylene chloride from Example 1). The addition of trimethylacetyl chloride was complete after 50 minutes; the temperature ranged between 37°–50° C. during the addition. The warm organic phase was separated and the aqueous phase was extracted with methylene chloride (2×100 ml). The combined methylene chloride solution was washed with 1 N HCl (2×100 ml), H₂O (3×200 ml), 10% NaCl (100 ml), and concentrated in vacuo (<25° C. at 30 mm) to give free flowing crystalline N-[(2-methyl)phenyl]-2,2-dimethylpropanamide. Final drying (at 60° C., 30 mm, 24 hours) gave N-[(2-methyl)phenyl]-2,2-dimethylpropanamide (379 g, 1.98 mol) in 99% yield. The melting point of the product was 108°–111° C. This product can be used directly in Example 3 without recrystallization.

EXAMPLE 3

Synthesis of N-[2-(2-hydroxy-2-phenylethyl)-phenyl]-2,2-dimethyl-propanamide

A stirred solution of N-[(2-methyl)phenyl]-2,2-dimethyl-propanamide (95.6 g, 0.5 mol) in THF (500 ml) was cooled to 0° C. and treated with 1.6 M n-butyl-lithium in hexane (628 ml, 0.1 mol). The addition of n-butyllithium was complete after 45 minutes. During the addition, the temperature of the mixture was maintained below 10° C. with external cooling. The resultant dianion solution was aged for 2 hours at 0° C. until the homogeneous orange solution became a yellow heterogeneous slurry. The dianion was then quenched with benzaldehyde (63.6 g, 0.6 mol) and aged for 15 minutes at about 24° C. The reaction mixture was diluted with ether (200 ml), treated with crushed ice (200 g), and stirred for 5 minutes. The organic phase was separated, washed with saturated sodium chloride (250 ml), dried over anhydrous magnesium sulfate, filtered and concentrated in vacuo. The residual oil was crystallized from hexane, filtered and recrystallized from dichloromethane (500 ml reflux) to give N-[2-(2-hydroxy-2-phenylethyl)-phenyl]-2,2-dimethylpropanamide (87 g, 0.29 mol) in 58% yield. The product had a melting point of 183°–184° C.

EXAMPLE 4

Synthesis of N-[2-(2-chloro-2-phenylethyl)phenyl]-2,2-dimethylpropanamide

N-[2-(2-hydroxy-2-phenylethyl)phenyl]-2,2-dimethylpropanamide (29.74 g, 0.1 mol) was partially dissolved in dichloromethane (120 ml). Thionyl chloride (12.69 g, 0.11 mol, 1.1 equiv.) was added over a 3-minute period to the resulting mixture. A substantially homogeneous solution formed with moderate evolution of hydrogen chloride and sulfur dioxide. The reaction mixture was maintained below 27° C. When evolution of gas ceased, the reaction mixture was worked up by washing the mixture with saturated sodium bicarbonate solution until the aqueous phase remained neutral (pH=6.5 to 7). The organic phase was separated, washed with saturated sodium chloride solution, dried over anhydrous magnesium sulfate, filtered and concentrated in vacuo to give 31.89 g of product. The product was purified by silica gel chromatography (CH₂Cl₂/hexane, 50:50; followed by CH₂Cl₂) to give a quantitative yield of an off-white crystalline product having a melting point of 87°–92° C.

EXAMPLE 5

Synthesis of N-[2-(2-methylamino-2-phenylethyl)phenyl]-2,2-dimethylpropanamide

N-[2-(2-chloro-2-phenylethyl)phenyl]-2,2-dimethyl-propanamide (1.0 g, 3.17 mol) was reacted with monomethyl amine (7 g of 40% aqueous solution) in 2-propanol (3 g). The mixture was heated to 80° C. and stirred for 1 hour. Formation of product was indicated by TLC (silica gel/70 ethyl acetate/30 methanol).

EXAMPLE 6

Synthesis of N-methyl-2-amino-α-phenylphenethylamine dihydrochloride (a) N-[2-(2-methylamino-2-phenylethyl-phenyl]-2,2-dimethyl-propanamide (62 g, 0.2 mol) was dissolved in 5 N HCl (124 g) and stirred under a nitrogen atmosphere at 100° C. for 24 hours. The warm reaction mixture (about 35°–40° C.) was extracted with toluene (2×100 ml) to effect recovery of trimethylacetic acid. The aqueous phase was dried by azeotropic distillation with toluene (200 ml) using a Dean-Stark phase separator. The product was collected by filtration, slurried in hot 2-propanol (200 ml), refiltered and dried in vacuo (30 mm) at 45° C. for 12 hours to give N-methyl-2-amino-α-phenylphenethylamine dihydrochloride (58.7 g, 0.196 mol) in 98% yield. The product had a melting point of 251°–253° C.

(b) N-[2-(2-methylamino-2-phenylethyl)phenyl]-2,2-dimethyl-propanamide (155 g, 0.5 mol) was dissolved in 6 N HCl (310 g) and stirred under a nitrogen atmosphere at 100° C. for 28 hours. The reaction mixture was cooled to 23° C. and toluene (200 ml) was added. Stirring was continued until the product had crystallized from the aqueous phase. The product was collected by filtration, washed with toluene (2×50 ml) and dried in vacuo (30 mm) at 60° C. for 60 hours to give N-methyl-2-amino-α-phenylphenethylamine dihydrochloride (139 g, 93% yield). The melting point of the product was 252°–254° C. The organic phase of the filtrate was concentrated in vacuo to give a 58% recovery of trimethylacetic acid. The aqueous phase of the filtrate afforded a second crop of N-methyl-2-amino-α-phenylphenethylamine dihydrochloride (9.3 g, 6%). The total yield of product was 99%.

EXAMPLE 7

Synthesis of 2,3-dimethyl-4-3H-1,3-benzodiazepin hydrochloride

A heterogeneous mixture of N-methyl-2-amino-α-phenylphenethylamine dihydrochloride (150 g, 0.5 mol) in acetonitrile (500 ml) was treated with triethylorthoacetate (202 ml, 1.1 mol) and heated to 70° C. for 2 hours with stirring under a dry nitrogen atmosphere. The reaction mixture was filtered, concentrated in vacuo, and the residual solid recrystallized from 2-propanol at −10° C. to give 2,3-dimethyl-4-phenyl-3H-1,3-benzodiazepin hydrochloride (118 g, 0.413 mol) in 83% yield. The product had a melting point of 239.5°–241° C.

EXAMPLE 8

Synthesis of
2,3-dimethyl-4-phenyl-3H-1,3-benzodiazepin (free base)

A heterogeneous mixture of the dihydrochloride salt of N-ethyl-2-amino-α-phenylphenethylamine (9 g, 0.03 mol) in acetonitrile (36 cc dried over 4 Å molecular sieves) was treated with triethylorthoacetate (9.73 g, 11 cc, 0.06 mol) and heated to 70° C. with stirring under a dry nitrogen atmosphere. At 50° C. (after about 15 minutes of heating) the reaction mixture became homogeneous. The reaction mixture was concentrated in vacuo and partitioned between 100 ml toluene and 50 ml 5% NaOH. The toluene phase was washed with 10% NaCl, dried over sodium sulfate, filtered and concentrated in vacuo to give a light yellow-brown solid product, which was shown by GC to be 96.7% 2,3-dimethyl-4-phenyl-3H-1,3-benzodiazepin. This crude product free base was recrystallized from 15 ml 2-propanol at 82° C., diluted with 30 ml hexane and dried at 45° C. (30 mm for 12 hours). 4.64 g (0.0185 mol) of product with a melting point of 144.5°–145.4° C. were obtained at a yield of 61.8%. A second crop was recrystallized from 5 ml 2-propanol, washed with 3 ml hexane and dried at 40° C. (30 mm for 12 hours). 1.92 g (0.0077 mol) of product with a melting point of 143.5°–144.5° C. were obtained at a yield of 25.6%. The mother liquor (0.64 g) from the first crop contained 0.24 g of product representing a yield of 3.2%.

EXAMPLE 9

Conversion of
2,3-dimethyl-4-phenyl-3H-1,3-benzodiazepin (free base)
to hydrochloride salt 1.9 g (0.0759 mol) of the free base 2,3-dimethyl-4-phenyl-3H-1,3-benzodiazepin was dissolved in 2-propanol and treated at 5°–10° C. with an excess of 2-propanol saturated with anhydrous HCl. The monohydrochloride salt of the 2,3-dimethyl-4-phenyl-3H-1,3-benzodiazepin was recrystallized from solution and recovered by filtration. The monohydrochloride salt had a melting point of 241°–242° C. The salt was dried (60° C., 30 mm, 24 hours) to yield 1.50 g of a white crystalline powder.

What is claimed is:

1. A compound of the formula

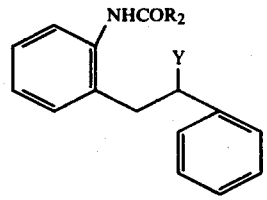

where Y is —OH; halogen;

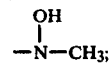

$R_1SO_3$—; where $R_1$ is a straight chain or branched chain alkyl group having 1 to 5 carbon atoms, or aryl; and $R_2$ is —C(CH$_3$)$_3$ or —OC(CH$_3$)$_3$.

2. A compound according to claim 1 wherein Y is —OH.

3. A compound according to claim 1 wherein Y is chlorine or bromine.

4. A compound according to claim 1 wherein Y is chlorine.

5. A compound according to claim 1 wherein Y is CH$_3$SO$_3$—.

6. A compound according to claim 1 wherein Y is a phenyl sulfonyloxy, a p-chlorophenyl sulfonyloxy or a p-toluene sulfonyloxy group.

7. A compound according to claim 1 wherein Y is

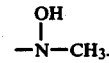

8. A compound according to claim 1, 2, 3, 4, 5, 6 or 7 in which $R_2$ is —C(CH$_3$)$_3$.

* * * * *